United States Patent [19]
Leonardi et al.

[11] Patent Number: 5,642,178
[45] Date of Patent: Jun. 24, 1997

[54] SPORTS EYEGLASSES WITH SOFT, RESILIENT CONNECTOR PADS

[76] Inventors: Peter F. Leonardi, Box 443, Old Peck Hill Rd., Gloversville, N.Y. 12078; Carmine S. Di Chiara, 23 Gregory La., Warren, N.J. 07059

[21] Appl. No.: 269,401

[22] Filed: Jun. 24, 1994

Related U.S. Application Data

[63] Continuation of Ser. No. 894,644, Jun. 5, 1992, abandoned.

[51] Int. Cl.$^6$ .................. G02C 3/02; G02C 5/16; A61F 9/02
[52] U.S. Cl. .......... 351/111; 351/121; 351/123; 351/156; 351/157; 2/411; 2/426; 2/431; 2/452
[58] Field of Search ................ 351/111, 121, 351/123, 142, 153, 156, 157; 2/426, 431, 448, 450, 452, 411, 439, 414; 16/228

[56] References Cited

U.S. PATENT DOCUMENTS

| | | |
|---|---|---|
| 2,406,608 | 8/1946 | Joyce ............................ 2/450 |
| 2,504,524 | 4/1950 | Hayward ........................ 2/452 |
| 2,545,428 | 3/1951 | Liautaud ........................ 2/14 |
| 2,755,803 | 7/1956 | Dorsey .......................... 2/426 |
| 3,173,147 | 3/1965 | Gross et al. ................... 2/452 |
| 4,229,837 | 10/1980 | Solari ........................... 2/439 |
| 4,264,987 | 5/1981 | Runckel ......................... 2/452 |
| 4,367,561 | 1/1983 | Solari ........................... 2/439 |
| 4,391,498 | 7/1983 | Rengstorff ..................... 351/153 |
| 4,515,449 | 5/1985 | Davidson ....................... 351/157 |
| 4,527,292 | 7/1985 | Kasama et al. ................. 2/452 |
| 4,556,995 | 12/1985 | Yamamoto ...................... 2/452 |
| 4,688,272 | 8/1987 | Leonardi ........................ 2/431 |
| 4,755,040 | 7/1988 | Haslbeck ....................... 351/43 |
| 4,886,349 | 12/1989 | Willis .......................... 351/114 |
| 4,978,209 | 12/1990 | Ohba ............................ 351/153 |
| 4,978,210 | 12/1990 | Lundbeck ....................... 351/157 |
| 4,998,815 | 3/1991 | Lin ............................. 2/450 |
| 5,016,293 | 5/1991 | Lickle .......................... 2/436 |
| 5,046,198 | 9/1991 | Hunnebeck ...................... 2/440 |
| 5,181,280 | 1/1993 | Zachry, Jr. .................... 2/452 |
| 5,189,447 | 2/1993 | Oleson .......................... 2/448 |
| 5,495,623 | 3/1996 | Leonardi ........................ 2/431 |

FOREIGN PATENT DOCUMENTS

| | | | |
|---|---|---|---|
| 611486 | 3/1935 | Austria ......................... | 2/452 |
| 8600012 | 1/1986 | WIPO ............................ | 351/114 |

*Primary Examiner*—Ricky D. Shafer
*Attorney, Agent, or Firm*—Roylance, Abrams, Berdo & Goodman, L.L.P.

[57] ABSTRACT

A pair of sports eyeglasses having a substantially hard, rigid frame, a pair of soft, resilient strap connector pads, and a headband assembly coupled to the rigid frame by the soft resilient strap connector pads. The soft connector pads provide cushioning at the junction between the rigid frame and the straps to provide a comfortable fit to the user. The frame front is shortened at its ends for use with helmets used in sporting activities or the like. The headband assembly includes a first elastic strap extending between the soft, resilient connector pads, a second strap coupled at its ends to the first strap and extending over the top of the user's head, and a third strap extending between the first and second straps along a rear portion of the wearer's head.

16 Claims, 2 Drawing Sheets

SPORTS EYEGLASSES WITH SOFT, RESILIENT CONNECTOR PADS

This is a continuation of application Ser. No. 07/894,644 filed Jun. 5, 1992, now abandoned.

FIELD OF THE INVENTION

This invention relates to sports eyeglasses with soft, resilient connector pads. More specifically, the invention relates to sports eyeglasses for use in sporting activities to prevent eye injury to a player from a ball, equipment, hands, or the like. The sports eyeglasses have a rigid frame coupled to a strap by a pair of soft, resilient connector pads for use in sporting activities requiring a helmet.

BACKGROUND OF THE INVENTION

In a large number of sporting activities, such as tennis, hand ball, squash, racket ball, basketball, soccer, football, hockey, and other sporting activities in which there is fast movement of players and the use of a ball or other physical contact, there is a continuing danger of a participant being struck in the eye by the ball, equipment or hand of an opponent. This can result in severe injury or even, in some cases, loss of an eye.

Thus, a variety of different types of protective eyewear has been developed for each of the variety of sporting activities. Generally, the protective eyewear are formed as either eyeglasses or goggles. These prior protective eyeglasses suffer from one or more deficiencies. For example, some protective eyewear cannot be worn with a helmet. Other protective eyewear is heavy and cumbersome to wear, which causes the wearer substantial discomfort during participation in the sporting event. Many others protective eyewear are very uncomfortable to wear since they are made of a very hard rigid plastic.

Examples of various prior devices relating to protective eyewear are disclosed in U.S. Pat. No. 2,406,608 to Joyce; U.S. Pat. No. 2,504,524 to Hayward; U.S. Pat. No. 2,755,803 to Dorsey; U.S. Pat. No. 2,545,428 to Liautaud; U.S. Pat. No. 4,229,837 to Solari; U.S. Pat. No. 4,367,561 to Solari; U.S. Pat. No. 4,688,272 to Leonardi; U.S. Pat. No. 5,016,293 to Lickle; U.S. Pat. No. 5,033,837 to Leonardi; and U.S. Pat. No. 5,046,198 to Hunnebeck.

In view of the above, it is apparent that there exists a need for protective eyewear which is comfortable to wear and can be used in almost any sporting activity. This invention addresses these needs in the art, along with other needs which will become apparent to those skilled in the art once given this disclosure.

SUMMARY OF THE INVENTION

Accordingly, an object of the invention is to provide sports eyeglasses with soft, resilient connector pads for coupling ends of a strap or headband to a rigid frame.

Another object of the invention is to provide a pair of sports eyeglasses for use with a helmet worn during sporting activities.

Another further object of the invention is to provide a pair of sports eyeglasses that are simple to manufacture, aesthetically pleasing, and not bulky.

Yet another object of the invention is to provide a pair of sports eyeglasses which are comfortable to wear.

The foregoing objects are basically obtained by providing a sports eyeglasses, the combination comprising: a rigid frame having a first end and a second end; a flexible strap having a first end and a second end; first soft, resilient connector member for coupling the first end of the frame to the first end of the strap, and for cushioning the first end of the frame; and a second soft, resilient connector member for coupling the second end of the frame to the second end of the strap, and for cushioning the second end of the frame.

Other objects, advantages and salient features of the invention will become apparent from the following detailed description, which, taken in conjunction with the annexed drawings, discloses a preferred embodiment of the invention.

BRIEF DESCRIPTION OF THE DRAWINGS

Referring now to the drawings which form part of this original disclosure.

DETAILED OF THE INVENTION

Figure 1:
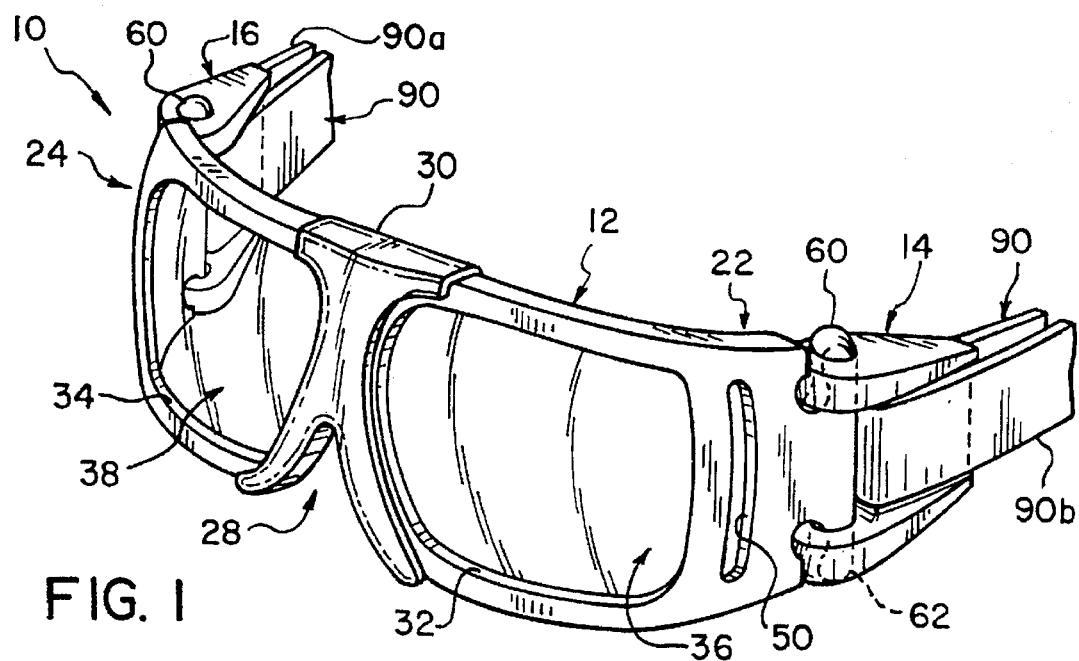
FIG. 1 is a right side perspective view of a pair of sports eyeglasses with a portion its headband or strap broken away for clarity in accordance with the present invention.
Figure 2:
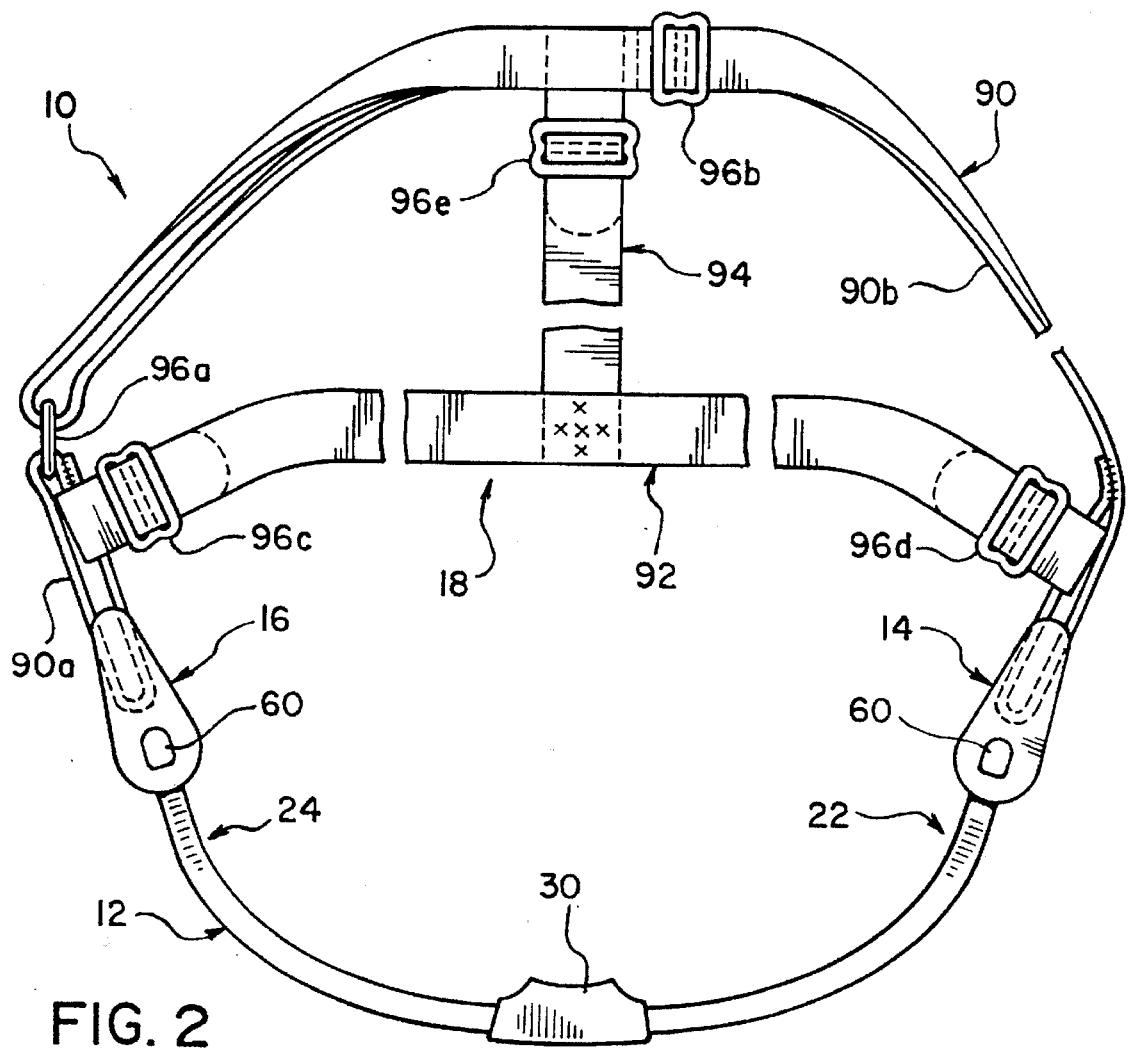
FIG. 2 is a top plan view of the sports eyeglasses of FIG. 1 with the complete headband assembly illustrated in accordance with the present invention.

As seen in FIGS. 1 and 2, a pair of sports eyeglasses 10 in accordance with the present invention is illustrated, and includes a substantially rigid frame 12, a first soft, resilient strap connector pad 14, a second soft, resilient strap connector pad 16, and a headband assembly 18 coupled to frame 12 via connector pads 14 and 16.

Frame 12 is integrally molded as a one-piece, unitary frame having a front portion 20, a first end portion 22 and a second end portion 24. The integrally molded frame 12 can be comprised of any material, but is advantageously comprised of a lightweight, moldable, shatterproof polymeric material, such as propionate, cellulose acetate, nylon or buterate.

Front portion 20 includes a centrally located nose-area recess 28 for receiving a wearer's nose, a pair of apertures 32 and 34, and a pair of lenses 36 and 38 retained in apertures 32 and 34. An optional resilient, nose and forehead pad 30 can be attached to front portion 20 at nose-area recess 28 in a conventional manner.

Each of the apertures 32 and 34 has a peripheral recess for retaining lenses 36 and 38 therein, respectively. Lenses 36 and 38 can be either refractive or non-refractive lenses as needed.

First end portion 22 and second end portion 24 are substantially identical, and thus, only first end portion 22 will be discussed and illustrated in detail.

Figure 3:
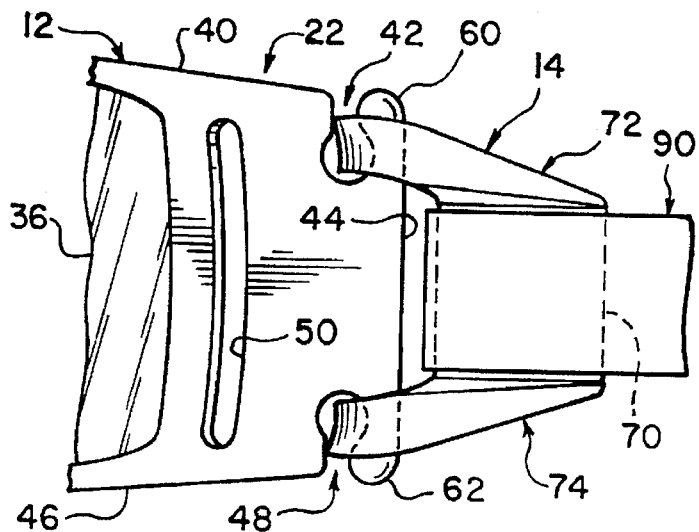
FIG. 3 is an enlarged, partial plan view of a first end of the sports eyeglasses of FIGS. 1 and 2.
Figure 4:
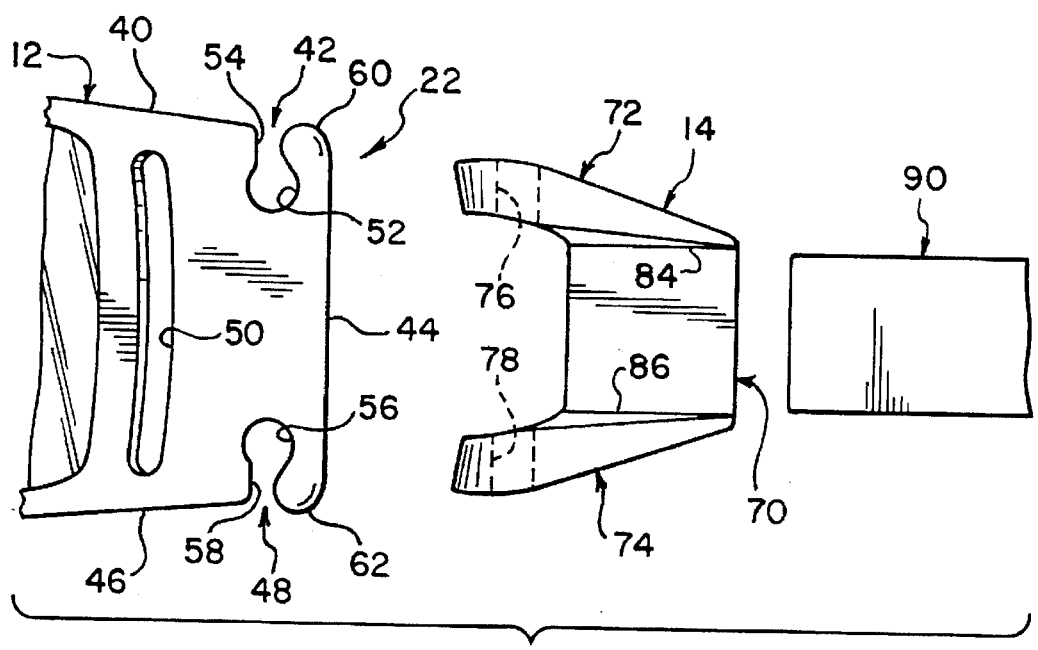
FIG. 4 is an exploded, enlarged, partial end elevational view of the sports eyeglasses of FIG. 3.

As seen in FIGS. 3 and 4, first end portion 22 includes an upper edge 40 with an upper cut out 42 extending inwardly therefrom, a free end edge 44 remotely located from front portion 20, a lower edge 46 with a lower cut out 48 extending inwardly therefrom, and an elongated slot 50 extending between upper edge 40 and lower edge 46 adjacent front portion 20.

First end portion 22 is integrally molded with front portion 20 and only extends approximately 1 inch rearwardly so that the substantially rigid, hard material of first end portion 22 does not interfere with a helmet used by a wearer in sporting activities or the like. Rather, a helmet used by a wearer will only engage connector pads 14 and 16 and headband assembly 18, which are both flexible so as not to interfere with the helmet.

Upper and lower cut outs 42 and 48 are substantially identical, except that upper cut out 42 opens upwardly, while lower cut out 48 opens downwardly. Cut out 42 includes a circular hole portion 52 and a connecting portion 54 extending between circular hole portion 52 and upper edge 40. Similarly, lower cut out 48 includes a circular hole portion 56 and a connecting portion 58 extending between circular hole portion 56 and lower edge 46.

Connecting portions 54 and 58 are slightly smaller in width than circular hole portions 52 and 56. Accordingly, upper cut out 42 forms a hook member 60 extending upwardly from free end 44 and curving towards the front portion 20 of frame 12. Likewise, lower cutout 48 forms a lower hook member 62 extending downwardly from free end 44 and curving towards front portion 20 of frame 12.

Figure 5:
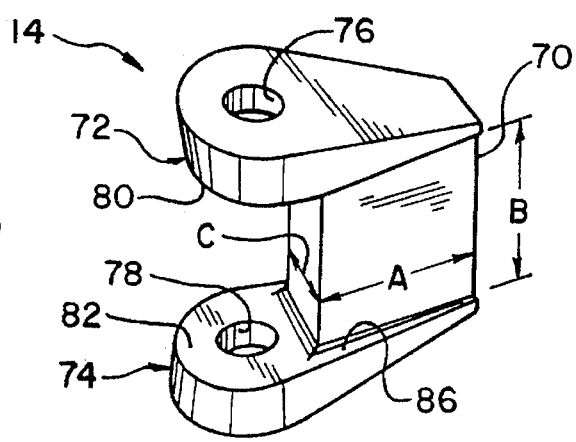
FIG. 5 is a top, side perspective view of one of the connector pads in accordance with the present invention.

Connector pads 14 and 16 are substantially identical, and thus only connector pad 14 will be described and illustrated in detail herein. As seen in FIGS. 4 and 5, connector pad 14 includes a center rectangular body portion 70 releasably coupled to headband assembly 18, an upper connecting arm 72 releasably coupled to hook member 60 of end portion 22, and a lower connecting arm 74 releasably coupled to hook member 62 of end portion 22. Connector pads 14 and 16 are integrally molded as a one-piece, unitary member from a soft, flexible, resilient rubber material. Preferably, both connector pad 14 and 16 are molded from a thermoplastic elastomer. A particularly advantageous material for connector pads 14 and 16 is a block copolymer of butadiene, isoprene and styrene having a durometer of 20–40, and preferably 20.

As seen in FIG. 4, rectangular body portion 70 has a horizontal width A of about ⅝ inch, a vertical height B of about ¾ inch and a thickness C of about ¼ inch. Body portion 70 is adapted to be encircled by a portion of headband assembly 18 as discussed below. (All future references to thickness are thicknesses in the direction parallel to that of thickness C as shown in FIG. 5.).

Upper and lower connecting arms 72 and 74 are substantially identical, except that they are mirror images of each other. Upper connecting arm 72 is integrally connected to the upper end of body portion 70, while lower connecting arm 74 is integrally connected to the lower end of body portion 70. Upper connecting arm 72 extends outwardly and substantially perpendicularly from body portion 70, and has a circular bore 76 for receiving hook member 60 therein. Lower arm 74 extends outwardly and substantially perpendicularly from the bottom edge of body portion 70, and has a circular bore 78 for receiving hook member 62 therein. Accordingly, body portion 70 along with arms 72 and 74 form U-shaped connector pad 14 with a portion of headband assembly 18 being received around body portion 70 and between arms 72 and 74.

Bores 76 and 78 of arms 72 and 74 are vertically spaced and axially aligned. The widths or diameters of bores 76 and 78 are preferably slightly smaller than the maximum width of hook members 60 and 62. Accordingly, upon insertion of hook members 60 and 62 into bores 76 and 78, respectively, bores 76 and 78 will dilate or expand outwardly to provide an interference fit therebetween. In other words, hook members 60 and 62 stretch bores 70 and 78 outwardly to insure a snug connection therebetween and to prevent accidental disengagement between frame 12 and strap connector pad 14. Thus, as seen in FIGS. 2–3, connector pads 14 and 16 are releasably coupled to first and second end portions 22 and 24 at first and second locations of frame 12 via hook members 60 and 62 engaging bores 76 and 78 of arms 72 and 74.

Moreover, the width of cut outs 42 and 48 along connecting portions 54 and 58 are slightly smaller than the maximum thickness of the portions of connecting arm 72 and 74 received in cut outs 42 and 48 as illustrated in FIG. 5. This further insures that frame 12 and connector pad 14 do not accidental separate from each other.

The opposed inner surfaces 80 and 82 of connecting arm 72 and 74, respectively, form ledges 84 and 86 at their intersection with body portion 70. Ledges 84 and 86 together with the adjoining surface of body portion 70 form a recess on each side of body portion 70 for receiving a portion of headband assembly 18 therein. Thus, the horizontal thicknesses of arms 72 and 74 (as represented by the letter T in FIG. 5) of connector pad 14 provide a cushion between end portion 22 of frame 12 and the temple of a wearer's head. In other words, the horizontal thicknesses of arms 72 and 74 of each of the connector pads 14 and 16, as seen in FIGS. 2–5, are greater than the horizontal thicknesses of the first and second end portions 22 and 24 at the first and second locations of frame 12, i.e., where the hook members 60 and 62 engage bores 76 and 78 of arms 72 and 74 of the connector pads 14 and 16. As seen in the figures, arms 72 and 74 of connector pads 14 and 16 each have a horizontal thickness at the first and second locations of frame 12, i.e., at hook members 60 and 62, such that arms 72 and 74 extend sufficiently outwardly from first and second end portions 22 and 24 of frame 12 towards the wearer's head to engage the wearer's head and to provide cushioning therebetween. Also, the arm 72 and 74 cushion the ends of the strap 90 of headband assembly 18 which encircles the body portions of connector pads 14 and 16. Accordingly, connector pads 14 and 16 provide cushioning at the temple areas of a wearer to prevent the hard, rigid material of frame 12 and the strap 90 of headband assembly 18 from contacting the wearer. Specifically, the arms 72 and 74 preferably have sufficient horizontal and vertical thicknesses to prevent the ends of strap 90 and end portions 22 and 24 of frame 12 from contacting the temples of the wearer's head. It should be readily apparent from this disclosure that the use of the words "horizontal" and "vertical", as used herein, are used to orient the structure of frame 12 and connector pads 14 and 16 relative to each other, when worn by the wearer.

Headband assembly 18 includes a first retaining strap 90 with its ends connected to strap connector pads 14 and 16, a second retaining strap 92 with its ends coupled to first retaining strap 90, and a third retaining strap 94 coupled to and extending between first retaining strap 90 and second retaining strap 92. Straps 90, 92 and 94 are preferably all flexible straps which are adjustable in length to accommodate various sizes of heads.

In particular, strap 90 is made of two-pieces of elastic, fabric strap elements 90a, and 90b, and has a pair of conventional flat, plastic buckles 96a and 96b attached thereto for adjusting the length of strap 90. As seen in FIG. 2, strap element 90a, has its ends sewn together to form a loop which encircles the body portion of connector pad 16 and a portion of buckle 96a.

Strap element 90b, has one end sewn to form a loop encircling body portion 70 of connector pad 14, and its other end fixedly coupled to buckle 96b thereto. Buckle 96b is also slidably coupled along strap element 90b, to form an adjustable loop slidably coupled to buckle 96a in a conventional manner.

Strap 92 extends over the top of the wearer's head, and is preferably a flexible, nonelastic strap made of any suitable material, such as nylon. Of course, strap 92 can be made of elastic material, if desired. Strap 92 also includes a pair of flat buckle 96c and 96d for adjusting the length of the ends of the second strap 92. In particular, buckle 96c is slidably coupled onto one end of strap 92 to form a first loop in a conventional manner for adjusting the end of strap 92. Preferably, the first looped end of strap 92 is looped around the looped strap element 90a, which is coupled to connector pad 16. Likewise, buckle 96d is slidably coupled onto the other end of strap 92 to form a second loop in a conventional manner for adjusting the end of strap 92. Preferably, the second looped end of strap 92 encircles the fixed loop of strap element 90b, which is coupled to connector pad 14.

Third strap 94 has one of its ends sewn to the center portion of strap 92, while its other end is looped around the center portion of strap 90 and adjustable coupled thereto via buckle 96e. Accordingly, third strap 94 extends over the back portion of the wearer's head between first and second straps 90 and 92. Preferably, strap 94 is formed of flexible, non elastic nylon material. Of course, strap 94 can be made of an elastic material, if desired.

Buckles 96a–96e are conventional flat plastic buckles similar to the buckles disclosed in U.S. Pat. No. 2,504,524 to Hayward, which is hereby incorporated herein by reference. Since buckles 96a–96e are conventional and well known, they will not be discussed or illustrated in detail herein.

In use, frame 12 is placed on the wearer's face with the wearer's nose received in nose recess 28. Then, strap 90 is stretch rearwardly away from frame 12 so as to be pulled over the wearers' head. Once frame 12 and headband assembly 18 are on the wearer's head, the first strap 90 will be stretched along the back of the wearer's head between connector pads 14 and 16, the second strap 92 will extend over the top of the wearer's head, and the third strap 94 will extend over the back of the wearer's head. The stretching of strap 90 will also cause pad connectors 14 and 16 to be stretched along with first strap 90 to provide a comfortable fit for the wearer.

While only one embodiment has been chosen to illustrate the invention, it will be understood by those skilled in the art that various changes and modifications can be made herein without departing from the scope of the invention as defined in the appended claims.

What is claimed is:

1. Sports eyeglasses, comprising:
   a substantially rigid frame having a front portion, a first end portion extending rearwardly from one end of said front portion and a second end portion extending rearwardly from an opposite end of said front portion;
   retaining means for retaining the eyeglasses on a wearer's head, and having a first end and a second end;
   first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and
   second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame,
   each of said first and second end portions of said frame having a first horizontal thickness at said first and second locations respectively, and each of said first ends of said first and second connector means having a second horizontal thickness greater than said first horizontal thickness at said first and second locations, respectively, with portions of said first and second connector means extending sufficiently outwardly from said first and second end portions of said frame at said first and second locations, respectively, toward the wearer's head to engage the wearer's head and to provide cushioning between said first and second end portions of said frame, respectively, and the wearer's head, said first and second connector means being formed of a thermoplastic elastomer.

2. Sports eyeglasses according to claim 1, wherein
   said first and second connector means are releasably coupled at their respective said first ends to said first and second end portions of said frame and at their respective said second ends to said first and second ends of said retaining means, respectively.

3. Sports eyeglasses according to claim 2, wherein
   each of said first and second end portions of said frame has a pair of oppositely extending hook members for engaging and coupling said first and second connector means thereto, respectively.

4. Sports eyeglasses according to claim 3, wherein
   each of said first and second connectors has a pair of spaced openings for receiving said pair of hook members of said first and second end portions of said frame therein, respectively.

5. Sports eyeglasses, comprising:
   a substantially rigid frame having a front portion, a first end portion extending rearwardly from one end of said front portion and a second end portion extending rearwardly from an opposite end of said front portion;
   retaining means for retaining the eyeglasses on a wearer's head, and having a first end and a second end;
   first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and
   second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame,
   each of said first and second end portions of said frame having a first horizontal thickness at said first and second locations respectively, and each of said first ends of said first and second connector means having a second horizontal thickness greater than said first horizontal thickness at said first and second locations, respectively, with portions of said first and second connector means extending sufficiently outwardly from said first and second end portions of said frame at said first and second locations, respectively, toward the wearer's head to engage the wearer's head and to provide cushioning between said first and second end portions of said frame, respectively, and the wearer's head; said first connector means being releasably coupled to said first end portion of said frame at said first end of said first connector means and said retaining means at said second end of said first connector means.

6. Sports eyeglasses according to claim 5, wherein said first end portion of said frame has a pair of oppositely extending hook members for engaging and coupling said first connector means thereto.

7. Sports eyeglasses according to claim 6, wherein said first connector means has a pair of spaced openings for receiving said pair of hook members therein, respectively.

8. Sports eyeglasses according to claim 5, wherein said retaining means includes a first strap formed of an elastic material.

9. Sports eyeglasses according to claim 8, wherein said retaining means further includes a second strap having its ends adjustably coupled to said first strap adjacent said first and second ends of said retaining means, respectively.

10. Sports eyeglasses according to claim 9, wherein said retaining means further includes a third strap having one end fixedly coupled to a center portion of said second strap and its other end adjustably coupled to a center portion of said first strap.

11. Sports eyeglasses, comprising:

a substantially rigid frame having a front portion, a first end portion extending rearwardly from one end of said front portion and a second end portion extending rearwardly from an opposite end of said front portion;

retaining means for retaining the eyeglasses on a wearer's head, and having a first end and a second end;

first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame, each of said first and second end portions of said frame having a first horizontal thickness at said first and second locations, respectively, and each of said first ends of said first and second connector means having a second horizontal thickness greater than said first horizontal thickness at said first and second locations respectively, with portions of said first and second connector means extending sufficiently outwardly from said first and second end portions of said frame at said first and second locations, respectively, toward the wearer's head to engage the wearer's head and to provide cushioning between said first and second end portions of said frame, respectively, and the wearer's head, said first end portion of said frame further having a pair of oppositely extending hook members, and said first connector means having a pair of spaced openings for receiving said pair of hook members therein, respectively, for releasably coupling said first connector means to said first end portion of said frame, said openings being smaller in width than said hook members to expand said openings when said hook members are received therein.

12. Sports eyeglasses according to claim 11, wherein said first and second connector means are formed of a thermoplastic elastomer.

13. Sports eyeglasses, comprising:

a substantially rigid frame having a front portion, a first end portion extending rearwardly from one end of said front portion and a second end portion extending rearwardly from an opposite end of said front portion;

retaining means for retaining the eyeglasses on a wearer's head, and having a first end and a second end;

first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame, each of said first and second end portions of said frame having a first horizontal thickness at said first and second locations, and each of said first ends of said first and second connector means having a second horizontal thickness greater than said first horizontal thickness at said first and second locations, respectively, with portions of said first and second connector means extending sufficiently outwardly from said first and second end portions of said frame, respectively, toward the wearer's head to engage the wearer's head and to provide cushioning between said first and second end portions of said frame at said first and second locations, respectively, and the wearer's head, each of said first and second end portions of said frame further having a pair of oppositely extending hook members, and each of said first and second connector means having a pair of spaced openings for receiving said pair of hook members therein, respectively, for releasably coupling said first and second connector means to said first and second end portions of said frame, said openings of said first and second connector means being smaller in width than said hook members to expand said openings when said hook members are received therein.

14. Sports eyeglasses, comprising:

a substantially rigid frame having a front portion, a first end portion extending rearwardly from one end of said front portion and a second end portion extending rearwardly from an opposite end of said front portion;

retaining means for retaining the eyeglasses on a wearer's head, and having a first end and a second end;

first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame, each of said first and second end portions of said frame having a first horizontal thickness at said first and second locations respectively, and each of said first ends of said first and second connector means having a second horizontal thickness greater than said first horizontal thickness at said first and second locations, respectively, with portions of said first and second connector means extending sufficiently outwardly from said first and second end portions of said frame at said first and second locations, respectively, toward the wearer's head to engage the wearer's head and to provide cushioning between said first and second end portions of said frame, respectively, and the wearer's head, said first and second end connector means having a durometer of 20–40.

15. Sports eyeglasses, comprising:

a substantially rigid frame having a front portion, a first end portion extending rearwardly from one end of said front portion and a second end portion extending rearwardly from an opposite end of said front portion;

retaining means for retaining the eyeglasses on a wearer's head, and having a first end and a second end;

first soft, resilient, cushioning connector means for coupling said first end portion of said frame to said first end of said retaining means, and for cushioning said first end portion of said frame, said first connector means having a first end coupled to said first end portion of said frame at a first location and a second end coupled to said first end of said retaining means and rearwardly spaced from said first end portion of said frame; and second soft, resilient, cushioning connector means for coupling said second end portion of said frame to said second end of said retaining means, and for cushioning said second end portion of said frame, said second connector means having a first end coupled to said second end portion of said frame at a second location and a second end coupled to said second end of said retaining means and rearwardly spaced from said second end portion of said frame, each of said first and second end portions of said frame having a first horizontal thickness at said first and second locations respectively, and each of said first ends of said first and second connector means having a second horizontal thickness greater than said first horizontal thickness at said first and second locations, respectively, with portions of said first and second connector means extending sufficiently outwardly from said first and second end portions of said frame at said first and second locations, respectively, toward the wearer's head to engage the wearer's head and to provide cushioning between said first and second end portions of said frame, respectively, and the wearer's head, each of said first and second connector means having a first side facing toward the wearer's head with a recess extending from said second end of each of said first and second connector means toward said first end of each of said first and second connector means, said recess having a depth for receiving a portion of said retaining means therein to provide cushioning between said retaining means and the wearer's head.

16. Sports eyeglasses, the combination comprising:

a substantially rigid frame having a front portion, a first end portion and a second end portion;

retaining means for retaining the eyeglasses on a wearer's head having a first end and a second end;

a first soft, resilient connector for coupling said first end portion of said frame to said first end of said retaining means, and for cushioning said first end portion of said frame; and a second soft, resilient connector for coupling said second end portion of said frame to said second end of said retaining means, and for cushioning said second end portion of said frame, said first and second connectors having a durometer of 20–40, and extending sufficiently outwardly from said first and second end portions, respectively, to engage the wearer's head.

* * * * *